US00PP30644P3

(12) United States Plant Patent
Heimovaara

(10) Patent No.: US PP30,644 P3
(45) Date of Patent: Jul. 2, 2019

(54) ***ALSTROEMERIA* PLANT NAMED 'ZAPRITAMA'**

(50) Latin Name: *Alstroemeria hybrida*
Varietal Denomination: Zapritama

(71) Applicant: Sjoukje Heimovaara, Oegstgeest (NL)

(72) Inventor: Sjoukje Heimovaara, Oegstgeest (NL)

(73) Assignee: Van Zanten Breeding B.V., Rijsenhout (NL)

( * ) Notice: Subject to any disclaimer, the term of this patent is extended or adjusted under 35 U.S.C. 154(b) by 0 days.

(21) Appl. No.: 15/732,756

(22) Filed: Dec. 23, 2017

(65) Prior Publication Data

US 2019/0069462 P1 Feb. 28, 2019

(51) Int. Cl.
*A01H 5/02* (2018.01)
*A01H 6/56* (2018.01)

(52) U.S. Cl.
USPC ..... Plt./309
CPC ..... *A01H 6/564* (2018.05)

(58) Field of Classification Search
USPC ..... Plt./309
See application file for complete search history.

(56) References Cited

PUBLICATIONS

UPOV hit on *Alstroemeria* plant named 'Zapritama', QZ PBR 2017/2084, Aug. 25, 2017.*

* cited by examiner

*Primary Examiner* — Anne Marie Grunberg
(74) *Attorney, Agent, or Firm* — C. A. Whealy

(57) ABSTRACT

A new and distinct cultivar of *Alstroemeria* plant named 'Zapritama', characterized by its compact, upright to outwardly spreading and uniformly mounded plant habit; moderately vigorous growth habit; numerous purple violet-colored flowers; and excellent container and garden performance.

2 Drawing Sheets

Botanical designation: *Alstroemeria hybrida.*
Cultivar denomination: 'ZAPRITAMA'.

BACKGROUND OF THE INVENTION

The present invention relates to a new and distinct cultivar of *Alstroemeria* plant, botanically known as *Alstroemeria hybrida*, commercially used as a potted and garden-type *Alstroemeria*, and hereinafter referred to by the name 'Zapritama'.

The new *Alstroemeria* plant is a product of a planned breeding program conducted by the Inventor in Rijsenhout, The Netherlands. The objective of the breeding program is to create new potted *Alstroemeria* plants with uniform plant habit, freely flowering habit, attractive leaf and flower coloration and good garden performance.

The new *Alstroemeria* plant originated from a cross-pollination made by the Inventor in Rijsenhout, The Netherlands in May, 2012 of a proprietary *Alstroemeria hybrida* selection identified as code number 15622-2, not patented, as the female, or seed, parent with a proprietary *Alstroemeria hybrida* selection identified as code number 1269-1, not patented, as the male, or pollen, parent. The new *Alstroemeria* plant was discovered and selected by the Inventor as a single flowering plant from within the progeny of the stated cross-pollination in a controlled greenhouse environment in Rijsenhout, The Netherlands in June, 2013.

Asexual reproduction of the new *Alstroemeria* plant by rhizome divisions in a controlled greenhouse environment in Rijsenhout, The Netherlands since September, 2013 has shown that the unique features of this new *Alstroemeria* plant are stable and reproduced true to type in successive generations.

SUMMARY OF THE INVENTION

Plants of the new *Alstroemeria* have not been observed under all possible combinations of environmental conditions and cultural practices. The phenotype may vary somewhat with variations in environmental conditions such as temperature and light intensity without, however, any variance in genotype. The following traits have been repeatedly observed and are determined to be the unique characteristics of 'Zapritama'. These characteristics in combination distinguish 'Zapritama' as a new and distinct *Alstroemeria* plant:

1. Compact, upright to outwardly spreading and uniformly mounded plant habit.
2. Moderately vigorous growth habit.
3. Numerous purple violet-colored flowers.
4. Excellent container and garden performance.

Plants of the new *Alstroemeria* can be compared to plants of the female parent selection. Plants of the new *Alstroemeria* differ from plants of the female parent selection primarily in flower color as plants of the female parent selection have red-colored flowers.

Plants of the new *Alstroemeria* can be compared to plants of the male parent selection. Plants of the new *Alstroemeria* differ from plants of the male parent selection primarily in flower color as plants of the male parent selection have pink-colored flowers.

Plants of the new *Alstroemeria* can be compared to plants of *Alstroemeria hybrida* 'Zaprilou', disclosed in U.S. Plant Pat. No. 21,011. In side-by-side comparisons, plants of the new *Alstroemeria* differ primarily from plants of 'Zaprilou' in flower color as plants of 'Zaprilou' have red purple-colored flowers.

BRIEF DESCRIPTION OF THE PHOTOGRAPHS

The accompanying colored photographs illustrate the overall appearance of the new *Alstroemeria* plant showing the colors as true as it is reasonably possible to obtain in colored reproductions of this type. Colors in the photographs may differ slightly from the color values cited in the detailed botanical description which accurately describe the colors of the new *Alstroemeria* plant.

The photograph on the first sheet is a top perspective view of a typical flowering plant of 'Zapritama'.

The photograph on the second sheet is a close-up view of typical flowers of 'Zapritama'.

DETAILED BOTANICAL DESCRIPTION

The aforementioned photographs and following observations and measurements describe plants of the new *Alstroemeria* grown during the spring in 14-cm containers in a glass-covered greenhouse in Rijsenhout, The Netherlands. During the production of the plants, day temperatures ranged from 15° C. to 25° C., night temperatures ranged from 10° C. to 15° C., soil temperatures averaged 14° C. and light levels averaged 5,000 lux. Plants were three months old when the photographs and description were taken. In the following description, color references are made to The Royal Horticultural Society Colour Chart, 2015 Edition, except where general terms of ordinary dictionary significance are used.

Botanical classification: *Alstroemeria hybrida* 'Zapritama'.

Parentage:

- *Female, or seed, parent.*—Proprietary *Alstroemeria hybrida* selection identified as code number 15622-2, not patented.
- *Male, or pollen, parent.*—Proprietary *Alstroemeria hybrida* selection identified as code number 1269-1, not patented.

Propagation:

- *Type.*—In vitro rhizogenesis.
- *Time to produce a rooted young plant, summer.*—About 40 days at temperatures of 16° C. to 25° C.
- *Time to produce a rooted young plant, winter.*—About 60 days at temperatures of 16° C. to 20° C.
- *Root description.*—Fibrous, fleshy, thick; color, close to 155D.
- *Rooting habit.*—Freely branching; medium density.
- *Rhizomes.*—Shape: Elongate; rounded. Length: About 10 cm to 30 cm. Diameter: About 3 mm to 10 mm. Texture: Smooth. Color: Close to 155D.

Plant description:

- *Plant and growth habit.*—Compact, upright to outwardly spreading and uniformly mounding plant habit; freely branching habit with about six primary lateral branches, dense and bushy appearance; moderately vigorous growth habit; moderate growth rate.
- *Plant height.*—About 28 cm.
- *Plant diameter (spread).*—About 38 cm.

Lateral branch description:

- *Length.*—About 20 cm.
- *Diameter.*—About 7 mm.
- *Internode length.*—About 1.5 cm.
- *Strength.*—Moderately strong.
- *Aspect.*—About 45° from vertical.
- *Texture and luster.*—Smooth, glabrous; semi-glossy.
- *Color, developing and fully developed.*—Close to 138C.

Leaf description:

- *Arrangement.*—Alternate; simple.
- *Length.*—About 7 cm to 10 cm.
- *Width.*—About 2.5 cm to 3 cm.
- *Shape.*—Elliptical.
- *Apex.*—Acute.
- *Base.*—Cuneate.
- *Margin.*—Entire.
- *Texture and luster, upper surface.*—Smooth, glabrous; semi-glossy.
- *Texture and luster, lower surface.*—Ribbed; matte.
- *Aspect.*—Upright to somewhat horizontal, twisting.
- *Venation pattern.*—Parallel.
- *Color.*—Developing leaves, upper surface: Close to 143C. Developing leaves, lower surface: Close to 139C. Fully expanded leaves, upper surface: Close to 138A; venation, close to 144D. Fully expanded leaves, lower surface: Close to N138B; venation, close to N144D.
- *Petioles.*—Length: About 2 cm to 3 cm. Diameter: About 3 mm to 4 mm. Texture and luster: Smooth, glabrous; matte. Strength: Low, flexible. Color, upper surface: Close to 138B to 138C. Color, lower surface: Close to 138A.

Flower description:

- *Flower type and habit.*—Single cup-shaped flowers arranged in compound umbels; flowers face upright to outwardly; perianth segments separate; freely flowering habit with about 24 to 28 flower buds and flowers per plant at one time.
- *Natural flowering season.*—Flowering continuous from the spring until the autumn in The Netherlands; early flowering habit, plants begin flowering about 70 to 80 days after planting.
- *Fragrance.*—None detected.
- *Flower longevity on the plant.*—About one week; flowers not persistent.
- *Flower buds.*—Length: About 3.5 cm to 3.7 cm. Diameter: About 1 cm to 1.2 cm. Shape: Roughly ovoid. Texture and luster: Smooth, glabrous; semi-glossy. Color: Close to 70A to 70B.
- *Umbel height.*—About 12 cm.
- *Umbel diameter.*—About 15 cm.
- *Flower diameter.*—About 6 cm.
- *Flower depth.*—About 5.5 cm.
- *Perianth.*—Arrangement: Six arranged in two whorls, each whorl with two lateral and one median segments. Inner perianth, lateral segments: Length: About 5.5 cm. Width: About 2.3 cm. Shape: Elliptical. Apex: Cuspidate. Base: Attenuate. Margin: Proximally, entire and distally, finely dentate. Texture and luster, upper surface: Smooth, glabrous; semi-glossy. Texture and luster, lower surface: Ribbed; matte. Color, when opening, upper surface: Proximally, close to N74C; mid-section, close to 155A; distally, close to NN78B. Color, when opening, lower surface: Proximally, close to 76D and distally, close to NN74B. Color, fully opened, upper surface: Proximally, close to N80D; mid-section, close to 155A; distally, close to N80A; stripes, close to 183A; with development, proximally, close to 91D and distally, close to 83D. Color, fully opened, lower surface: Proximally, close to 77D; mid-section, close to 76D; distally, close to N78B; with development, proximally, close to 91D and distally, close to N87C. Inner perianth, median segment: Length: About 5 cm. Width: About 2 cm. Shape: Elliptical. Apex: Cuspidate. Base: Attenuate. Margin: Proximally, entire and distally, finely dentate. Texture and luster, upper surface: Smooth, glabrous; semi-glossy. Texture and luster, lower surface: Ribbed; matte. Color, when opening, upper surface: Close to NN78B to NN78D. Color, when opening, lower surface: Close to NN74B to NN74D. Color, fully opened, upper surface: Proximally, close to N80D and distally, close to N80A; with development, proximally, close to 91D and distally, close to 83D. Color, fully opened, lower surface: Proximally, close to 77D and distally, close to N78B; with development, proximally, close to 91C and distally, close to N87C. Outer perianth, lateral segments: Length: About 5.5 cm. Width: About 4 cm. Shape: Obovate. Apex: Wishbone-shaped. Base: Attenuate. Margin: Proximally, entire and distally, finely dentate. Texture and luster, upper surface: Ribbed; semi-glossy. Texture and luster, lower surface: Ribbed; matte. Color, when opening, upper surface: Proximally, close to N74C and distally, close to NN78B. Color, when opening, lower surface: Proximally, close to 76D and distally, close to NN74B. Color, fully opened, upper surface: Proximally, close to N80D and distally, close to N80A; with development, color becoming closer to N88B. Color, fully opened, lower surface: Proximally, close to N78C and distally, close to N78B; with development, color becoming closer to 83C. Outer perianth, median segment: Length: About 5.5 cm. Width: About 4 cm. Shape: Obovate. Apex: Wishbone-shaped. Base: Attenuate. Margin: Proximally, entire and distally, finely dentate. Texture and luster, upper surface: Ribbed; semi-glossy. Texture and luster, lower surface: Ribbed; matte. Color, when opening, upper surface: Proximally, close to N74C and distally, close to NN78B. Color, when opening, lower surface: Proximally, close to 76D and distally, close to NN74B. Color, fully opened, upper surface: Proximally, close to N80D and distally, close to N80A; with development, color becoming closer to N88B. Color, fully opened, lower surface: Proximally, close to N78C and distally, close to N78B; with development, color becoming closer to 83C.

*Pedicels*.—Length: About 1 cm. Diameter: About 4 mm. Strength: Strong. Angle: About 30° from vertical. Texture and luster: Smooth, glabrous; matte. Color: Close to 138B.

*Reproductive organs*.—Stamens: Quantity per flower: Typically six. Filament length: About 4 cm. Filament color: Close to N80D. Anther size: About 0.8 mm by 2 mm. Anther color: Close to N77A. Pollen amount: Abundant. Pollen color: Close to N187B. Pistils: Quantity per flower: One. Style length: About 3 cm. Style color: Close to N78C. Stigma diameter: About 0.7 mm. Stigma shape: Three-parted. Stigma color: Close to 76D. Ovary color: Close to 139C.

*Fruits and seeds*.—Fruit and seed development have not been observed on plants of the new *Alstroemeria* to date.

Disease & pest resistance: Plants of the new *Alstroemeria* have not been observed to be resistant to pathogens and pests common to *Alstroemeria* plants to date.

Garden performance: Plants of the new *Alstroemeria* have been observed to have excellent garden performance and to tolerate wind, rain and temperatures from about −5° C. to about 40° C.

It is claimed:

1. A new and distinct *Alstroemeria* plant named 'Zapritama' as illustrated and described.

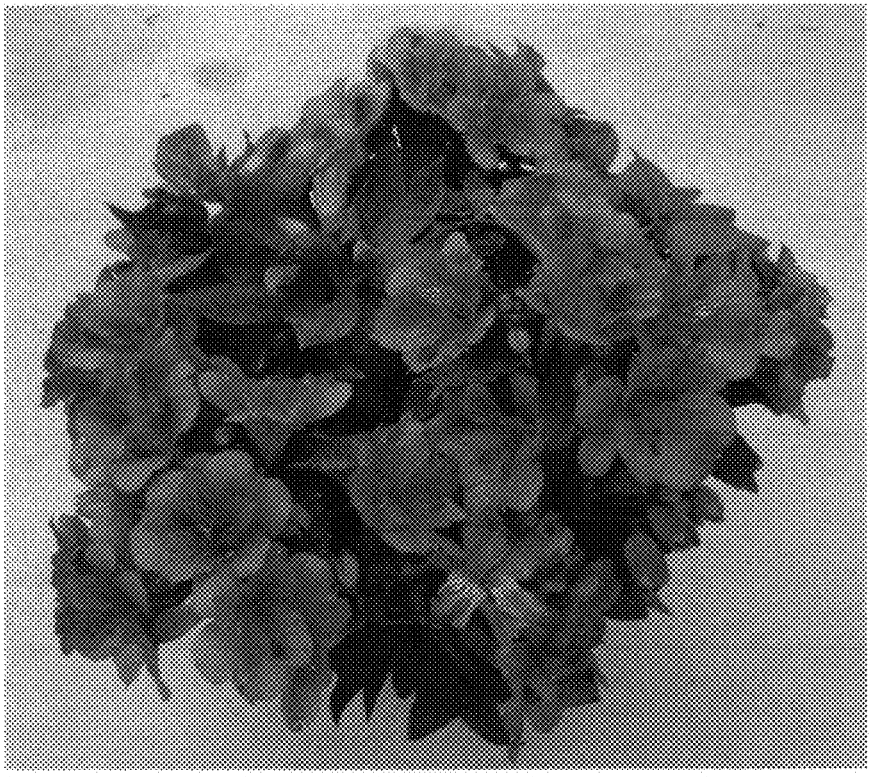

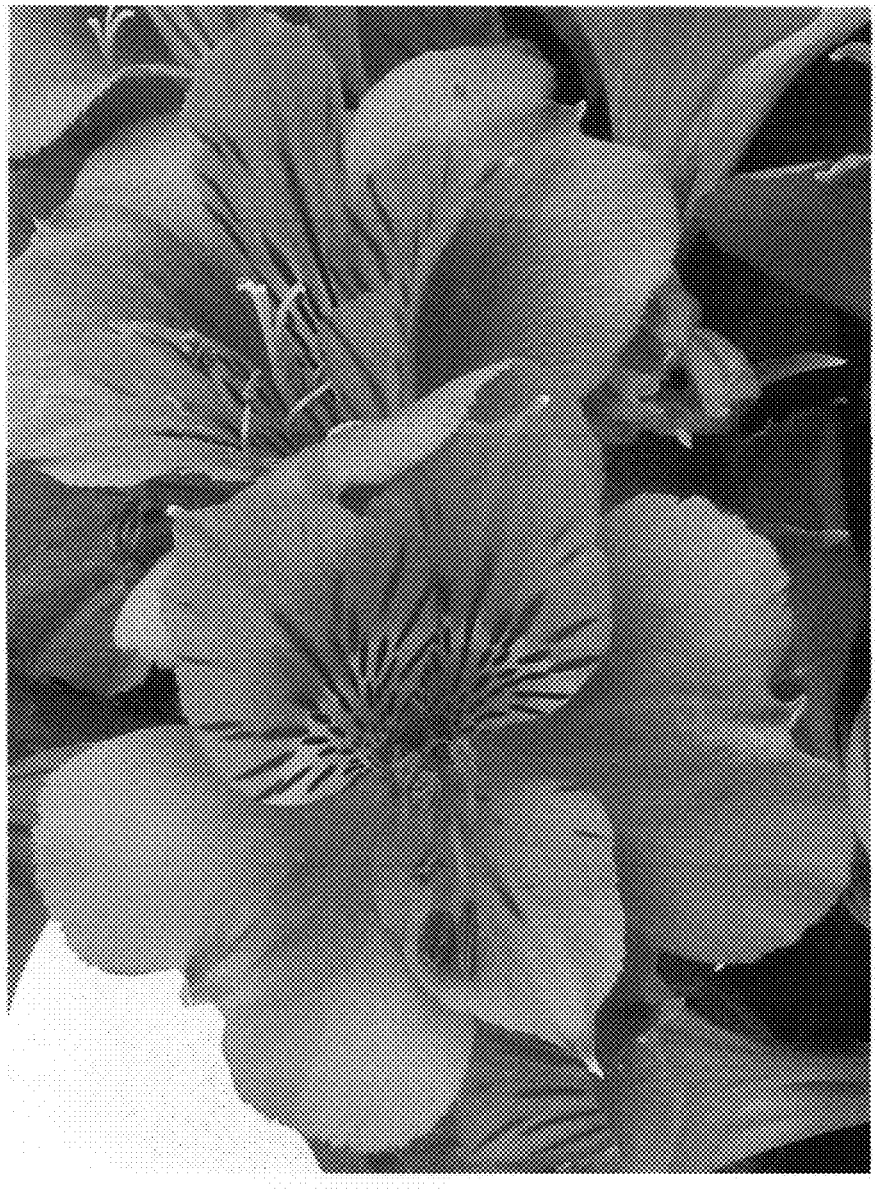

* * * * *